United States Patent [19]
Schwab et al.

[11] Patent Number: 5,769,819
[45] Date of Patent: Jun. 23, 1998

[54] CATHETER DISTAL TIP COMPONENT

[75] Inventors: Sharon Schwab; Maritess E. Minas, both of San Diego, Calif.

[73] Assignee: Medtronic, Inc., Minneapolis, Minn.

[21] Appl. No.: 839,998

[22] Filed: Apr. 24, 1997

[51] Int. Cl.$^6$ .................................................. A61M 29/00
[52] U.S. Cl. ............................................. 604/103; 604/96
[58] Field of Search ...................... 604/96–103; 606/192, 606/194

[56]  References Cited

U.S. PATENT DOCUMENTS

| | | | |
|---|---|---|---|
| 4,543,087 | 9/1985 | Sommercorn et al. | 604/43 |
| 4,702,252 | 10/1987 | Brooks et al. | 604/103 X |
| 4,787,388 | 11/1988 | Hofmann | 128/344 |
| 4,798,586 | 1/1989 | Stevens | 604/96 |
| 4,820,349 | 4/1989 | Saab | 128/344 |
| 4,877,031 | 10/1989 | Conway et al. | 128/344 |
| 4,921,483 | 5/1990 | Wijay et al. | 604/96 |
| 5,047,045 | 9/1991 | Arney et al. | 606/194 |
| 5,209,728 | 5/1993 | Kraus et al. | 604/96 |
| 5,290,230 | 3/1994 | Ainsworth et al. | 604/96 |
| 5,304,134 | 4/1994 | Kraus et al. | 604/96 |
| 5,344,402 | 9/1994 | Crocker | 604/96 |
| 5,370,615 | 12/1994 | Johnson | 604/96 |
| 5,569,196 | 10/1996 | Muni et al. | 604/96 |
| B1 4,739,768 | 11/1994 | Engleson | 128/658 |

FOREIGN PATENT DOCUMENTS 0184314  6/1986  European Pat. Off. ....... A61M 29/02

OTHER PUBLICATIONS

U.S. application No. 08/312,359, Ma, filed Sep. 26, 1994.
U.S. application No. 08/572,908, Fugoso et al., filed Dec. 15, 1995.

*Primary Examiner*—Corrine M. McDermott
*Attorney, Agent, or Firm*—Dianne M. F. Plunkett; Harold R. Patton

[57]  ABSTRACT

Disclosed is a medical catheter comprising a guidewire shaft defining a guidewire lumen. A distal tip extension defines a distal tip extension lumen having at a proximal end thereof a distal end of the guidewire shaft sealingly affixed therein. The inflatable balloon has a body portion, a tail portion and a cone shaped portion. The cone-shaped portion extends between the distal end of the body portion and the proximal end of the tail portion. The balloon tail portion is sealingly affixed to the distal tip extension such that the proximal end of the distal tip extension extends proximally from the proximal end of the balloon tail portion, the distal end of the distal tip extension extends distally from the distal end of the balloon tail and the distal end of the guidewire shaft is in alignment with the proximal end of the balloon tail portion.

22 Claims, 2 Drawing Sheets

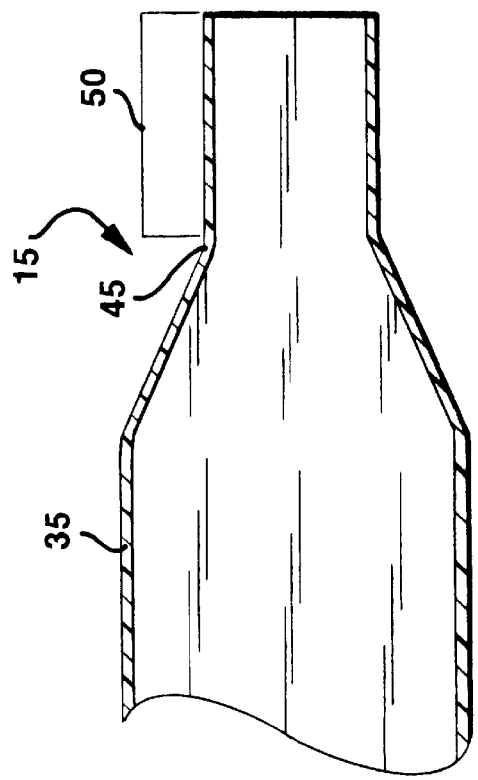
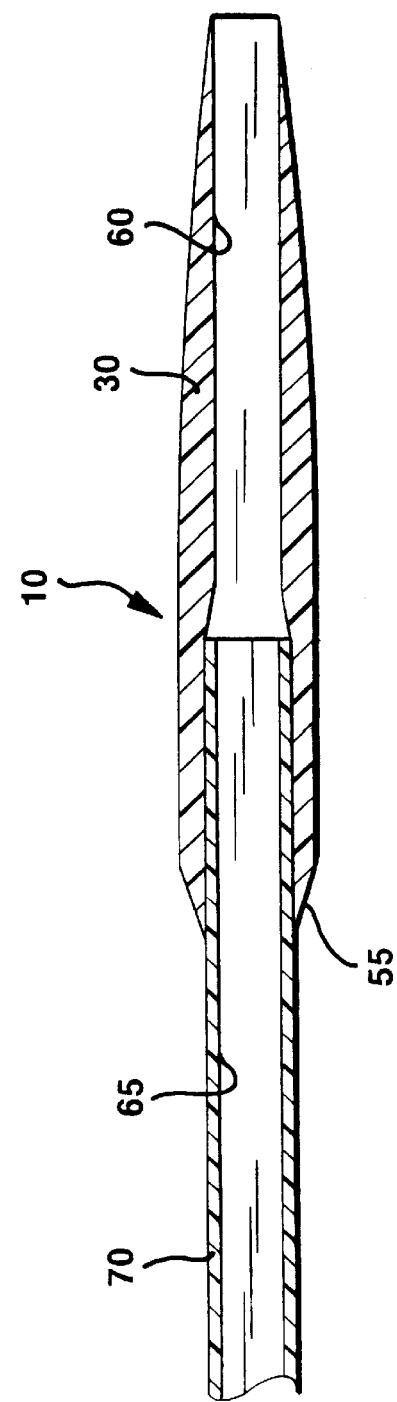

CATHETER DISTAL TIP COMPONENT

FIELD OF THE INVENTION

The present invention relates to angioplasty catheters, and more particularly, to a balloon catheter distal tip component which has high trackability and a low profile for use with any balloon materials including a semi compliant or a stiff high pressure balloon material.

BACKGROUND OF THE INVENTION

One of the therapeutic procedures applicable to the present invention is known as percutaneous transluminal coronary angioplasty (PTCA). This procedure can be used, for example, to reduce arterial build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The original catheter can then be withdrawn and a catheter of a different size or another device such as an atherectomy device can be inserted.

A biocompatible metal stent props open blocked coronary arteries, keeping them from reclosing after balloon angioplasty. A balloon of appropriate size and pressure is first used to open the lesion. The process is repeated with a stent crimped on a high pressure balloon. The stent is deployed when the balloon is inflated.

Conventional angioplasty balloons fall into high, medium, and low pressure ranges. Low pressure balloons are those that have burst pressures below 6 atmospheres ($6.1 \times 10^5$ Pascals). Medium pressure balloons are those that have burst pressures between 6 and 12 atm ($6.1 \times 10^5$ and $1.2 \times 10^6$ Pa). High pressure balloons are those that have burst pressures above 12 atm ($1.2 \times 10^6$ Pa). Burst pressure is determined by such factors as material selection, wall thickness and tensile strength, for example.

High pressure balloons are desirable because they have the ability to exert more force and crack hard lesions. High pressure balloons are also useful in stent deployment. because the stent must be forced against the artery's interior wall so that it will fully expand thereby precluding the ends of the stent from hanging down into the channel encouraging the formation of thrombus. The disadvantage of high pressure balloon materials such as PET and PET blends are that they are stiff and deflate flat with little or no rewrap which can result in winging and stent dislodgment when the balloon is withdrawn from the stent. High pressure balloon materials tend to be noncompliant materials. Noncompliant balloon materials grow on a flat curve to a fixed point and do not grow beyond that point.

Semicompliant balloon materials are those which fall into the medium pressure ranges and also into the low end of the high pressure ranges. Examples are Nylon and Nylon blends. Semicompliant balloon materials have a controlled growth between a specified range of pressures. Semicompliant materials are also more supple with greater flexibility which results in better lesion crossing ability, better rewrap and better tracking.

U.S. Pat. No. 4,739,768 to Engelson for "Catheter for Guidewire Tracking" discloses a drug delivery catheter with a relatively stiff proximal segment and a relatively flexible distal segment that is at least 5 cm long and can be advanced along a guidewire. While the distal segment itself may be very flexible, it is too long and flexible to achieve pushability sufficient enough to push through a blockage in the artery or stenosis.

U.S. Pat. No. 4,921,483 to Wijay et al. for an "Angioplasty Catheter" discloses a separate tip component wherein "[it] is an object of the invention use material such as nylon, polyvinylchloride and polyurethane".

Commonly owned, copending patent application Ser. No. 08/312,359 to Schwab (formerly Ma) for "Catheter Flexible Distal Tip" discloses a tip formed from the distal end of the balloon material distally extending beyond the guidewire lumen.

Commonly owned, copending patent application Ser. No. 08/572,908 to Fugoso et al. for "High Pressure Balloon Tip" discloses a guidewire shaft extending distal to the distal end of the balloon with a guidewire shaft step down area beginning just proximal to the distal end of the balloon. Adhesive begins proximal to the distal end of the balloon and fills between the inner diameter of the balloon and the outer diameter of the guidewire shaft tapering down to the outer diameter of the guidewire shaft.

Catheter balloons are designed for different purposes and formed from different materials and processes. Some materials are not optimal for balloon tips. An example is the polyethylene terephthalate (PET) balloon material typically used for high pressure balloons. This material results in a stiff, therefore low trackability, tip which resists rewrapping. What is needed is a catheter balloon which can withstand internal pressure of at least 325 psi without leaking or rupturing, which has a tip which is flexible, has high trackability, and has a low profile regardless of the material the balloon is made of.

SUMMARY OF THE INVENTION

The above features and advantages of the present invention, as well as others, are accomplished by providing a medical catheter comprising a guidewire shaft defining a guidewire lumen and a distal tip extension defining a distal tip extension lumen having at a proximal end thereof a distal end of the guidewire shaft sealingly affixed therein. The inflatable balloon has a body portion, a tail portion and a cone shaped portion. The cone-shaped portion extends between the distal end of the body portion and the proximal end of the tail portion. The balloon tail portion is sealingly affixed to the distal tip extension such that the proximal end of the distal tip extension extends proximally from the proximal end of the balloon tail portion, the distal end of the distal tip extension extends distally from the distal end of the balloon tail and the distal end of the guidewire shaft is in alignment with the proximal end of the balloon tail portion.

BRIEF DESCRIPTION OF THE DRAWINGS

FIG. 2 is a longitudinal cross-section of the balloon sub assembly; and

FIG. 3 is a longitudinal cross-section of the tip sub assembly.

DETAILED DESCRIPTION OF THE PREFERRED EMBODIMENTS

Figure 1:
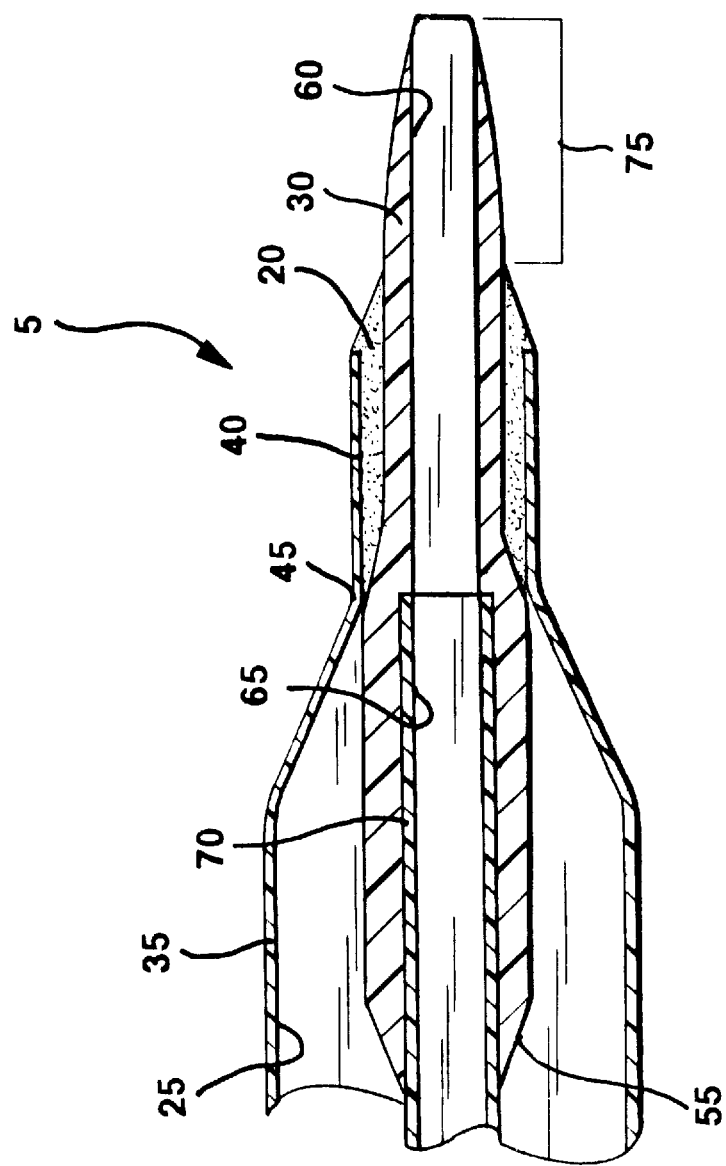
FIG. 1 is a longitudinal cross section of the distal tip of the balloon of the present invention.

The present invention is designed to give the advantages of a high performance, flexible, high trackability, low profile tip for balloon catheters regardless of the balloon material used. This is made possible by having a separate flexible, low profile tip component 10 which can be attached to a balloon of any material. The flexibility of the separate tip compensates for the stiffness of the balloon material. The separate tip component 10 could be optimized for flexibility or for profile by material selection, configuration, dimensions or length. The balloon 35 material could be independently optimized for characteristics such as pressure, compliance, perfusion etc. By attaching the separate tip component 10 made of a flexible material such as LDPE to a balloon 35 made of stiff material such as PET, the leading edge of the catheter will still be flexible enough to negotiate tortuous paths and enter tight lesions. Once the tip has entered the lesion or navigated through the curve, the pushability of the catheter will result in the balloon 35 following the tip component 10 into the lesion or around the curve. The present invention provides a catheter balloon tip that can reliably withstand internal pressures of at least 325 psi without leaking or rupturing and which is relatively easy, consistent and reliable to manufacture.

FIG. 1 is a longitudinal cross-sectional view of a high pressure balloon catheter tip 5 adapted for use in percutaneous transluminal coronary angioplasty (PTCA). The balloon subassembly 15 is seen in FIG. 2. The balloon 35 can be made of any material suitable for any pressure; this includes high pressure balloons which are made from materials such as PET or PET blends, medium pressure balloons which are made from materials such as Nylon or Nylon blends, and low pressure balloons which are made from materials such as Linear Density Polyethylene (LDPE). Any suitable balloon 35 material, however, could be used from the elastomeric family, from the semi-crystalline family or from multiple material, coextruded, multilayered materials.

The balloon 35 distal tail 50 is trimmed to between about 1.5 mm to 2.5 mm and should define a lumen inner diameter of approximately 0.020–0.028 inches. For 3.0 mm diameter balloons of 20 mm in length, a distal tail 50 inner diameter of 0.025–0.028 inches is preferred. The stiffer the balloon 35 material, the shorter the distal tail 50 should be. For a blend of PET and 10% Ethylene-vinyl acetate copolymer (EVA) a distal tail 50 length of 2.5 mm is preferable. This distal tail 50 length is also preferable for a blend such as Nylon 11 and 5% Surlyn. The balloon 35 can be formed into any shape such as, spiral, double, perfusion or any conventional shape etc.

The tip component 10 subassembly is seen in FIG. 3. The same tip component 10 can be used for all balloon 35 sizes. The tip component 10 subassembly is comprised of a guidewire shaft 70 and a distal tip extension 30. The guidewire shaft 70 is made from High Density Polyethylene (HDPE) tubing although other materials of similar durometer and flexibility may also be used. The guidewire shaft 70 typically has dimensions suitable for a standard 0.014 inch guidewire such as, for example, a 0.017 inch inner diameter, a 0.023 inch outer diameter and approximately 150 cm in length.

The distal 2.0–3.5 mm of the distal tip extension 30 is shaved to form the distal shave 75. This tapers down distally to an outer diameter of approximately 0.017 to 0.021 inches, or the inner diameter of the guidewire lumen. The length of the shaved area is a function of the thickness of the tubing wall. Thinner wall thicknesses require a shorter shave to avoid kinking. The distal shave 75 portion begins approximately 1.0 mm to 1.5 mm distal to the adhesive fillet 20. The proximal end of the distal tip extension 30 is shaved to form the proximal shave 55. The proximal shave 55 tapers down proximally for a length of approximately 0.5 mm to 1.5 mm for ease of insertion of the distal tip extension 30 into the balloon inflation lumen 25 and also to reduce the profile and avoid an abrupt transition. Other methods which could be used to achieve the taper include radio frequency (RF) welding or compressive heat bonding where the tip may simultaneously be molded into the final or nearly final shape.

The distal tip extension 30 is preferably made from semi-crystalline materials such as LDPE although any semi-crystalline or elastomeric material could be used. An advantage of applicant's tip design is that relatively stiff balloon 35 materials (such as PET, PET blends, Nylon or Nylon blends) can be selected without foregoing flexibility because the balloon 35 material stiffness is offset by the high flexibility of the material used in the distal tip extension 30.

Assemble the tip 5 as follows. Begin with a 0.0165 inch mandrel within the guidewire shaft lumen 65. Select an LDPE distal tip extension 30 tube having an average wall thickness of between approximately 0.006 inches to 0.008 inches and more preferably 0.0075 inches. This recommended distal tip extension 30 wall thickness is important to achieving the required flexibility when using a combination such as, LDPE for the distal tip extension 30 and a stiffer balloon 35 material such as PET or nylon. Expand the distal tip extension 30 tube sufficiently by conventional means so that the guidewire shaft 70 can fit into the distal tip extension lumen 60. Insert the distal end of the guidewire shaft 70 and mandrel into the proximal end of the distal tip extension lumen 60. The overlapping area of the guidewire shaft 70 distal end and the distal tip extension 30 proximal end should be approximately 1.0 mm to 3.0 mm. Heat bond the overlapping area of the guidewire shaft 70 and the distal tip extension 30 together to form the tip component 10. Heat bonding assumes that the materials are melt compatible. If the materials are not melt compatible an adhesive or other bonding method such as laser bonding may be used. Heat shrink the distal portion of the distal tip extension 30 extending beyond the distal end of the guidewire shaft 70 down to the mandrel to reduce the outer diameter of the distal end of the distal tip extension 30 for that portion of the distal tip extension 30 which will lie beneath the balloon distal tail 50.

Insert the proximal end of the tip component 10 into the distal end of the balloon inflation lumen 25. The distal end of the guidewire shaft 70 should align with the balloon distal neck 45. The purpose of this alignment is to reduce the profile of the balloon distal tail 50 which then has but one layer within the distal tip extension 30 under the distal tail 50 as opposed to two layers including the distal tip extension 30 as well as the guidewire shaft 70. Although aligning the distal end of the guidewire shaft 70 (which is within the distal tip extension 30) with the proximal end of the distal tail 50 is the preferred embodiment, the guidewire shaft 70 distal end could also be aligned proximal to or distal to the proximal end of the distal tail 50.

The distal end of the distal tip extension 30 extends out of the distal end of the balloon 35 and the proximal end of the guidewire shaft 70 extends out of the proximal end of the balloon 35. The length of the overlap of the guidewire shaft 70 and the distal tip extension 30 is a function of the materials used in the guidewire shaft 70, distal tip extension and balloon 35. When using a blend of Nylon 11 and 5% Surlyn for the balloon 35 material, the overlap of the distal end of the guidewire shaft 70 and the proximal end of the distal tip extension 30 should be about 2 mm. The longer this overlap, the greater the reinforcement to the bond and thus the greater the reliability and strength of the bond. The bonded area between the distal tip extension 30 and the guidewire shaft 70 could be extended to mid balloon 35 and beyond. Bond the proximal end of the balloon 35 to the guidewire shaft 70 using any conventional means.

The proximal end of the distal tip extension 30 could also be butt bonded to the distal end of the guidewire shaft 70. The advantage of a butt bond compared to an overlapping joint are that of more flexibility and also of a smaller profile. The butt bond could also be encapsulated with a band of adhesive for reinforcement. The two materials butt bonded together must be melt compatible or a third tie layer must be used.

Adhesively bond 40 the overlapping area between the balloon distal tail 50 and the of the distal tip extension 30. The length of bond 40 may be varied based on the required reliability. Generally the longer the bond 40, the stronger the bond will be. Bond 40 may be as short at 0.5 mm and may extend to the balloon distal neck 45. A bond 40 length of 2.0 mm is preferable given a PET/10% EVA balloon and a LDPE distal tip extension 30. This bond 40 length is also suitable for blends such as Nylon 11 and 5% Surlyn. Typical bond 40 lengths will range between 1.5 mm and 2.5 mm. A shorter bond may not be suitable for higher pressures and a longer bond may be unnecessary. A preferred adhesive can be used such as a two part polyurethane available from HB Fuller of St. Paul, Minn. (part number UR 0531A/B). Other adhesives which could be used include cyanoacrylates such as Loctite® 4061 manufactured by Loctite Corp. in Hartford Conn., as well as ultraviolet cured adhesives or epoxies.

The tip component is finished by adding a distal bond adhesive fillet 20 of approximately 0.5 mm to 1.0 mm in length. The purpose of the fillet 20 is to eliminate the abrupt transition due to the difference in outer diameter and the difference in material flexibility between the balloon distal tail 50 and the distal tip extension 30. An adhesive can be used such as a urethane adhesive available from HB Fuller of St. Paul, Minn. (part number UR 0531A/B). Other bonding methods may be used in addition to heat or adhesives, including laser and RF welding.

The preceding specific embodiments are illustrative of the practice of the invention. It is to be understood, however, that other expedients known to those skilled in the art or disclosed herein, may be employed without departing from the appended claims.

No. Component
5 Balloon Catheter Tip
10 Tip Component
15 Balloon subassembly
20 Distal Bond Adhesive Fillet
25 Inflation Lumen
30 Distal Tip Extension
35 Balloon
40 Adhesive Bond
45 Balloon Distal Neck
50 Balloon Distal Tail
55 Proximal Shave
60 Distal Tip Extension Lumen
65 Guidewire Lumen
70 Guidewire Shaft
75 Distal Shave

What is claimed is:

1. A medical catheter comprising:
   a guidewire shaft having a proximal end and a distal end, the guidewire shaft defining a guidewire lumen sized to accommodate a guidewire;
   a distal tip extension having a proximal end, a distal end and an intermediate portion, the intermediate portion located between the proximal end and the distal end of the distal tip extension, the distal tip extension defining a distal tip extension lumen sized to accommodate a guidewire;
   the distal tip extension having at the proximal end thereof, the distal end of the guidewire shaft sealingly affixed therein;
   an inflatable balloon comprising:
     a body portion having a proximal end and a distal end;
     a tail portion having a proximal end, a distal end; and
     a cone shaped portion, the cone shaped portion extending between the distal end of the body portion and the proximal end of the tail portion, the tail portion being sealingly affixed to the distal tip extension such that the proximal end of the distal tip extension extends proximally from the proximal end of the tail portion;
   the distal end of the distal tip extension extends distally from the distal end of the tail portion;
   the distal tip extension includes a tapered portion located between the intermediate portion of the distal tip extension and the distal end of the distal tip extension; and
   wherein the tail portion is sealingly affixed at the tapered portion of the distal tip extension.

2. The medical catheter of claim 1 wherein the proximal end of the distal tip extension extends proximally into the balloon.

3. The medical catheter of claim 1 wherein the proximal end of the distal tip extension extends through the cone-shaped portion and into the body portion.

4. The medical catheter of claim 1 wherein the distal tip extension is comprised of a more flexible material than the guidewire shaft.

5. The medical catheter of claim 1 wherein the distal tip extension is comprised of a more flexible material than the balloon.

6. The medical catheter of claim 1 wherein the distal tip extension is comprised of linear density polyethylene.

7. The medical catheter of claim 6 wherein the distal tip extension has a wall thickness of between approximately 0.006 inches to 0.008 inches.

8. The medical catheter of claim 1 wherein the balloon is comprised of a material selected from the group consisting of polyethylene terephthalate and nylon.

9. A medical catheter comprising:
   a guidewire shaft having a proximal end and a distal end, the guidewire shaft defining a guidewire lumen sized to accommodate a guidewire;
   a distal tip extension having a proximal end, a distal end and an intermediate portion, the intermediate portion located between the proximal end and the distal end of the distal tip extension, the distal tip extension defining a distal tip extension lumen sized to accommodate a guidewire;
   the distal tip extension having at the proximal end thereof, the distal end of the guidewire shaft sealingly affixed therein;
   an inflatable balloon comprising:
     a body portion having a proximal end and a distal end;
     a tail portion having a proximal end, a distal end; and
     a cone shaped portion, the cone shaped portion extending between the distal end of the body portion and the proximal end of the tail portion, the tail portion being sealingly affixed to the distal tip extension such that the proximal end of the distal tip extension extends proximally from the proximal end of the tail portion;

wherein the distal tip extension intermediate portion has a proximate portion and a distal portion, the proximate portion has a first outer diameter and the distal portion has a second, smaller outer diameter; and wherein the tail portion is sealingly affixed to the distal tip extension at the second outer diameter.

10. A medical catheter comprising:

a guidewire shaft having a proximal end and a distal end, the guidewire shaft defining a guidewire lumen sized to accommodate a guidewire;

a distal tip extension having a proximal end, a distal end and an intermediate portion, the intermediate portion located between the proximal end and the distal end of the distal tip extension, the distal tip extension defining a distal tip extension lumen sized to accommodate a guidewire;

the distal tip extension having at the proximal end thereof, the distal end of the guidewire shaft sealingly affixed therein;

an inflatable balloon comprising:
a body portion having a proximal end and a distal end;
a tail portion having a proximal end a distal end; and
a cone shaped portion, the cone shaped portion extending between the distal end of the body portion and the proximal end of the tail portion, the tail portion being sealingly affixed to the distal tip extension such that the proximal end of the distal tip extension extends proximally from the proximal end of the tail portion; and wherein the distal tip extension lumen is larger at the proximal end of the distal tip extension than at the distal end of the distal tip extension.

11. A medical catheter comprising:

a guidewire shaft having a proximal end and a distal end, the guidewire shaft defining a guidewire lumen sized to accommodate a guidewire;

a distal tip extension having a proximal end, a distal end and an intermediate portion, the intermediate portion located between the proximal end and the distal end of the distal tip extension, the distal tip extension defining a distal tip extension lumen sized to accommodate a guidewire;

the distal tip extension having at the proximal end thereof, the distal end of the guidewire shaft sealingly affixed therein;

an inflatable balloon comprising:
a body portion having a proximal end and a distal end;
a tail portion having a proximal end, a distal end; and
a cone shaped portion, the cone shaped portion extending between the distal end of the body portion and the proximal end of the tail portion the tail portion being sealingly affixed to the distal tip extension such that the proximal end of the distal tip extension extends proximally from the proximal end of the tail portion; and wherein the distal tip extension outer diameter tapers from the intermediate portion thereof to the proximal end thereof.

12. A medical catheter comprising:

a guidewire shaft having a proximal end and a distal end, the guidewire shaft defining a guidewire lumen sized to accommodate a guidewire;

a distal tip extension having a proximal end, a distal end and an intermediate portion, the intermediate portion located between the proximal end and the distal end of the distal tip extension, the distal tip extension defining a distal tip extension lumen sized to accommodate a guidewire;

the distal tip extension having at the proximal end thereof, the distal end of the guidewire shaft sealingly affixed therein;

an inflatable balloon comprising:
a body portion having a proximal end and a distal end;
a tail portion having a proximal end, a distal end; and
a cone shaped portion, the cone shaped portion extending between the distal end of the body portion and the proximal end of the tail portion, the tail portion being sealingly affixed to the distal tip extension such that the proximal end of the distal tip extension extends proximally from the proximal end of the tail portion;

wherein the tail portion is sealingly affixed to the distal tip extension by an adhesive; and wherein the adhesive is shaped into a taper at the distal end of the tail portion.

13. A medical catheter comprising:

a guidewire shaft having a proximal end and a distal end, the guidewire shaft defining a guidewire lumen sized to accommodate a guidewire;

a distal tip extension having a proximal end, a distal end and an intermediate portion, the intermediate portion located between the proximal end and the distal end of the distal tip extension, the distal tip extension defining a distal tip extension lumen sized to accommodate a guidewire;

the distal tip extension having at the proximal end thereof, the distal end of the guidewire shaft sealingly affixed therein;

an inflatable balloon comprising:
a body portion having a proximal end and a distal end;
a tail portion having a proximal end a distal end; and
a cone shaped portion, the cone shaped portion extending between the distal end of the body portion and the proximal end of the tail portion, the tail portion being sealingly affixed to the distal tip extension such that the proximal end of the distal tip extension extends proximally from the proximal end of the tail portion; and wherein the distal end of the guidewire shaft is in alignment with the proximal end of the tail portion.

14. A medical catheter comprising:

a guidewire shaft having a proximal end and a distal end, the guidewire shaft defining a guidewire lumen sized to accommodate a guidewire;

a distal tip extension having a proximal end and a distal end, the distal tip extension defining a distal tip extension lumen sized to accommodate a guidewire;

the distal tip extension having an intermediate portion which includes a proximate intermediate portion with a first outer diameter, the distal tip extension having a distal intermediate portion with a second, smaller outer diameter and the distal end of the guidewire shaft sealingly affixed within the proximal end of the distal tip extension; and an inflatable balloon comprising:
a body portion having a proximal end and a distal end;
a tail portion having a proximal end and a distal end; and
a cone shaped portion, the cone-shaped portion extending between the distal end of the body portion and the proximal end of the tail portion, the tail portion sealingly affixed to the distal tip extension at the second, smaller diameter at the distal intermediate portion such that the proximal end of the distal tip extension extends proximally from the proximal end of the tail portion, the distal end of the distal tip extension extends distally from the distal end of the tail portion and the distal end of the guidewire shaft is in alignment with the proximal end of the tail portion.

15. The medical catheter of claim 14 wherein the distal tip extension has an outer diameter which tapers from the intermediate portion to the proximal end.

16. The medical catheter of claim 14 wherein the proximal end of the distal tip extension extends proximally into the balloon such that it extends through the cone-shaped portion and into the body portion.

17. The medical catheter of claim 14 wherein the tail portion is sealingly affixed to the distal tip extension by an adhesive.

18. The medical catheter of claim 14 wherein the adhesive is shaped into a taper at the distal end of the tail portion.

19. The medical catheter of claim 14 wherein the distal tip extension is comprised of a more flexible material than the guidewire shaft.

20. The medical catheter of claim 14 wherein the distal tip extension is comprised of linear density polyethylene.

21. The medical catheter of claim 20 wherein the distal tip extension has a wall thickness of between approximately 0.006 inches to 0.008 inches.

22. The medical catheter of claim 14 wherein the balloon is comprised of a material selected from the group consisting of polyethylene terephthalate and nylon.

* * * * *